(12) United States Patent
Pellerin et al.

(10) Patent No.: US 9,313,464 B2
(45) Date of Patent: Apr. 12, 2016

(54) CHECKING DEVICE AND METHOD BASED ON IMAGE PROCESSING

(75) Inventors: Florent Pellerin, Antibes (FR); Jacques Dumarest, Notre Dame de Mesage (FR)

(73) Assignee: STMICROELECTRONICS (GRENOBLE2) SAS, Grenoble (FR)

( * ) Notice: Subject to any disclaimer, the term of this patent is extended or adjusted under 35 U.S.C. 154(b) by 386 days.

(21) Appl. No.: 13/808,954

(22) PCT Filed: Jul. 11, 2011

(86) PCT No.: PCT/EP2011/061726
§ 371 (c)(1),
(2), (4) Date: Feb. 20, 2013

(87) PCT Pub. No.: WO2012/007411
PCT Pub. Date: Jan. 19, 2012

(65) Prior Publication Data
US 2013/0169798 A1    Jul. 4, 2013

(30) Foreign Application Priority Data
Jul. 16, 2010 (FR) .................................... 10 55787

(51) Int. Cl.
*H04N 7/12* (2006.01)
*H04N 5/228* (2006.01)
*A61J 7/00* (2006.01)
*G06F 17/00* (2006.01)
(Continued)

(52) U.S. Cl.
CPC ............ *H04N 7/183* (2013.01); *G06F 19/3462* (2013.01); *G07F 9/026* (2013.01); *G07F 17/0092* (2013.01); *G07G 1/0036* (2013.01); *A61J 7/04* (2013.01)

(58) Field of Classification Search
CPC ............ H04N 7/12; H04N 5/228; A61J 7/00; G06F 17/00; G03B 21/00; G03B 17/02
See application file for complete search history.

(56) References Cited

U.S. PATENT DOCUMENTS 6,304,797 B1   10/2001   Shusterman
7,210,598 B2 *   5/2007   Gerold et al. ................. 221/123
(Continued)

FOREIGN PATENT DOCUMENTS

EP   1161933 A2   12/2001

OTHER PUBLICATIONS

International Search Report and Written Opinion for PCT/EP2011/061726 mailed Aug. 26, 2011 (11 pages).
French Search Report and Written Opinion for FR 1055787 mailed Mar. 11, 2011 (8 pages).

*Primary Examiner* — Sath V Perungavoor
*Assistant Examiner* — Patricia I Young
(74) *Attorney, Agent, or Firm* — Gardere Wynne Sewell LLP

(57) ABSTRACT

A device for detecting objects includes a vessel intended to contain the objects. A sensor is configured to capture at least one image of the vessel. A processing device is configured to process at least one captured image by detecting objects of the at least one captured image, extracting characteristics of each detected object, and generating a list of the characteristics of each detected object. A memory stores the generated list, the memory also configured to store a first reference list of object characteristics. The processing device further generates a second list of characteristics from a captured image. The characteristics of each object of the second list are compared with, respectively, the characteristics of each object of the reference list.

22 Claims, 5 Drawing Sheets

(51) Int. Cl.
*G03B 21/00* (2006.01)
*B65D 83/04* (2006.01)
*H04N 7/18* (2006.01)
*G06F 19/00* (2011.01)
*G07F 9/02* (2006.01)
*G07F 17/00* (2006.01)
*G07G 1/00* (2006.01)
*A61J 7/04* (2006.01)

(56) References Cited

U.S. PATENT DOCUMENTS

| | | |
|---|---|---|
| 7,466,912 B2 * | 12/2008 | Ishikawa et al. ............... 396/539 |
| 2006/0119798 A1 * | 6/2006 | Huddleston et al. ............ 353/42 |
| 2006/0146532 A1 * | 7/2006 | Austreng et al. ............... 362/248 |
| 2008/0119958 A1 | 5/2008 | Bear et al. |
| 2009/0097704 A1 * | 4/2009 | Savidge et al. ............... 382/103 |

* cited by examiner

CHECKING DEVICE AND METHOD BASED ON IMAGE PROCESSING

PRIORITY CLAIM

This application is a 371 filing of PCT/EP2011/061726 filed Jul. 11, 2011, which claims priority from French Application for Patent No. 1055787 filed Jul. 16, 2010, the disclosures of which are hereby incorporated by reference.

TECHNICAL FIELD

The invention relates to checking based on image processing and more particularly checking the taking of objects. The invention applies advantageously but in a nonlimiting way to checking the taking of medicines.

BACKGROUND

In the state of the art, there are a number of solutions for checking the taking of medicines.

The patent application FR2650426, the disclosure of which is hereby incorporated by reference, describes a system with drawers containing medicines. This system has liquid crystal screens for displaying prescriptions and an alarm for notifying the patient of the time to take medicines.

The patent application FR 2717681, the disclosure of which is hereby incorporated by reference, describes a device with a casing provided with alarms, these alarms being set by virtue of the control keys.

The patent application EP1453466, the disclosure of which is hereby incorporated by reference, describes a storage device that makes it possible to take medicines according to posology. This device comprises a weekly doser, an inclined plane, and semi-inclined daily dosers.

The patent application FR 2841360, the disclosure of which is hereby incorporated by reference, describes a checking device in which a prescription is transmitted by mobile telephone, the transmission being secured by the use of the telephone number and of the code of the vital card. There is also provided a validation of the compatibilities of the medicines by virtue of an exchange of data between the mobile telephone and a central file which contains the data relating to the incompatibilities and the images of the medicines.

The patent application FR2920297, the disclosure of which is hereby incorporated by reference, describes a system comprising cells sealed by a sheet comprising an electrical continuity rupture device for detecting that the cell has been opened.

The international application WO 2009/023858, the disclosure of which is hereby incorporated by reference, relates to the management of a medication using mobile telephones. It comprises a management program capable of identifying and authenticating input/output images of the medication so as to confirm a correct medication performed by the patient.

The international application WO 2008/085607, the disclosure of which is hereby incorporated by reference, describes a device for dispensing medicines comprising a remote control system. This device comprises: compartments for storing the medicines, an image capture appliance positioned to capture an image of the interior of each compartment, a communication module for transmitting the captured image to a central control station.

In these documents, there is no provision for a system for checking the taking of medicines by a patient which is incorporated in the appliance for dispensing these medicines. Also, in these documents, the check is performed remotely and it does not make it possible to perform a check in real time for a better reliability of the checking system.

SUMMARY

According to one implementation and embodiment, there is proposed a standalone system for checking dispensing that does not entail exchanges with a central station.

According to another implementation and embodiment, there is proposed a real time checking system that is simple and that can be implemented inexpensively.

In particular, there is proposed a checking system which is suitable for elderly people, or handicapped people who have heavy medication.

According to one aspect, there is proposed a device for detecting objects, in particular forming a portable element that is capable, for example, of being carried in the pocket of a user, comprising a vessel intended to contain the objects to be detected, means for capturing at least one image of the vessel, and means for processing said at least one captured image.

The processing means comprise detection means for detecting objects of said at least one captured image, extraction means for extracting characteristics of each detected object, generation means for generating a list of the characteristics of each detected object and a memory for storing said generated list, the memory also being configured to store a first reference list of object characteristics and the processing means also being capable of generating a second list of characteristics from a captured image, the detection device also comprising means for comparing objects configured to compare the characteristics of each object of the second list with, respectively, the characteristics of each object of the reference list.

Thus, a device is provided which can be portable to be transported about the person easily. Furthermore, such a device is standalone energy-wise because it can be fitted with a built-in battery. It is also standalone in its operation because it does not necessarily have to be fitted with connection means. It also does not have to be remotely controlled from the outside.

The processing means are also capable of generating said reference list from a captured reference image.

According to one embodiment, the extraction means comprise segmentation means configured to segment the unrecognized objects out of the detected objects and perform a second object detection for each unrecognized object.

According to another embodiment, the memory is configured to store a list of characteristics of known objects, and the segmentation means also comprise shape recognition means configured to compare the characteristics of each detected object with, respectively, the characteristics of each known object in order to identify the recognized objects out of the detected objects.

According to yet another embodiment, the device comprises signaling means configured to signal the result of the comparison obtained from the comparison means.

The processing means can also comprise background detection means capable of detecting if at least one object is present within the vessel in a captured image.

The computation resources are not used unnecessarily to make a recognition if no object is detected.

The device may also comprise control means capable of interrupting the processing means in the case where no object is detected within the vessel.

The processing means may also comprise means for preprocessing the captured image.

According to another embodiment, the vessel has a dark and matt bottom.

The dark color makes it possible for the medicines to be distinguished more easily from the background. The matt tint provides a reduction of the glare which could be confused with the medicines. Thus, the detection of the background and of the objects are more accurate.

The vessel may also have a bottom comprising a number of identical patterns.

The identical reproduction of a pattern with a spatial frequency makes it possible to improve the detection of the bottom of the vessel.

Moreover, the vessel may have a relief bottom to prevent medicines from being stacked one on top of the other.

The device may also comprise means for displacing the objects contained in the vessel, such as vibrators that can be actuated, for example, by the user.

In another embodiment, the vessel comprises a transparent bottom, the device comprising lighting means arranged under the vessel and configured to light the vessel through its transparent bottom.

The device may also comprise an optical system, for enabling said means for capturing at least one image of the vessel to capture an image of said objects to be captured.

The device may be configured in size and in weight to make it portable.

The device may comprise means for wedging the objects in said vessel.

According to another aspect, there is proposed a use of the device defined hereinabove, as pill dispenser containing medicines forming said objects to be detected.

According to yet another aspect, there is proposed a method for detecting objects contained in a vessel, in which at least one image of the vessel is captured and said at least one captured image is processed.

According to a general characteristic of this aspect, the processing comprises a detection of the objects of said at least one image, an extraction of the characteristics of each detected object, a generation of a list of the characteristics of each detected object and a storage of said list of the characteristics, this method also comprising the storage of a first reference list of object characteristics, a capture of an image, a processing of said captured image so as to store a second list of characteristics, and a comparison of objects comprising a comparison of the characteristics of each object of the second list with, respectively, the characteristics of each object of the reference list.

The method is pyramidal, in the sense that the same simple processing is performed on each of the detected regions of the image and for each of the regions, a more complex processing is provided. The more complex processing also comprises the implementation of the same simple processing on segmented regions of the image. Furthermore, making a comparison on a list of extracted characteristics and not directly on the image allows for a simple, accurate and rapid comparison.

According to one implementation, the method comprises a capture of a reference image, a processing of said reference image so as to store said reference list of characteristics.

According to another implementation, the processing comprises a segmentation of the unrecognized objects, out of the detected objects, and a second object detection for each unrecognized object.

According to another implementation, the method comprises a storage of a list of characteristics of known objects, and the processing also comprises a shape recognition comprising a comparison of the characteristics of each detected object with, respectively, the characteristics of each known object, in order to identify the recognized objects out of the detected objects.

According to another implementation, the method comprises a signaling of the result of the comparison obtained from the comparison step.

According to yet another implementation, the method also comprises a first signaling if at least one object of said image captured so as to store a second list of characteristics is unrecognized, and a second signaling if, following a comparison of the characteristics of each object of the second list with, respectively, the characteristics of each object of the reference list, at least one object of the second list is different from the objects of the reference list.

According to yet another implementation, the method comprises a displacement of the objects contained in the vessel following said first signaling, a capture of a new image, a processing of said new captured image so as to store a new list of characteristics, and a comparison of objects comprising a comparison of the characteristics of each object of the new list with, respectively, the characteristics of each object of the reference list.

According to another implementation, the method comprises a capture of another image of the vessel, a processing of said other captured image, the processing comprising a detection of the background of the vessel and a third signaling if at least one object is detected within the vessel in said other processed image.

The processing may comprise a detection of the background of the vessel and is interrupted in the case where no object is detected within the vessel.

The processing may also comprise a step for preprocessing said at least one captured image.

Thus, the subsequent steps are simpler because the image is processed beforehand to reduce the number of calculations made during subsequent processing operations. This preprocessing step also makes it possible to improve the relevance of the results obtained during subsequent processing operations.

BRIEF DESCRIPTION OF THE DRAWINGS

Other advantages and features of the invention will become apparent from studying the detailed description of implementations and embodiments which are in no way limiting, and the appended drawings in which.

DETAILED DESCRIPTION OF THE DRAWINGS

Figure 1:
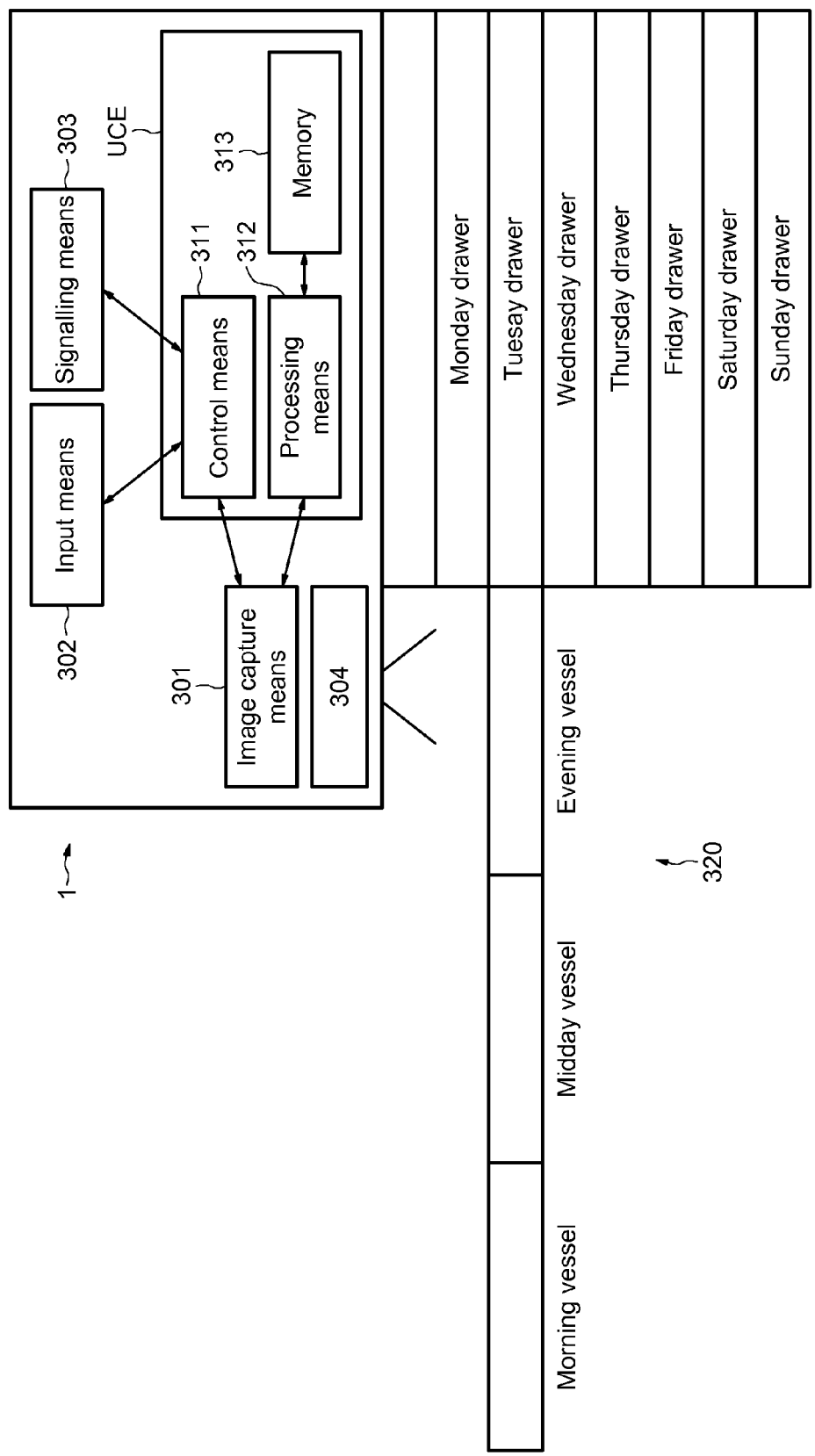
FIG. 1 illustrates one embodiment of an object detection device according to the invention.

FIG. 1 represents an object detection device 1 comprising at least one vessel 320, or pill dispenser, for receiving objects, in particular medicines. This object detection device 1 comprises image capture means 301, input means 302, signaling means 303, and an electronic control unit ECU, such as, for example, a microprocessor.

This ECU comprises control means 311, processing means 312 and a memory 313. The role of each of these elements is described in the following FIGS. 2 to 4.

Figure 2:
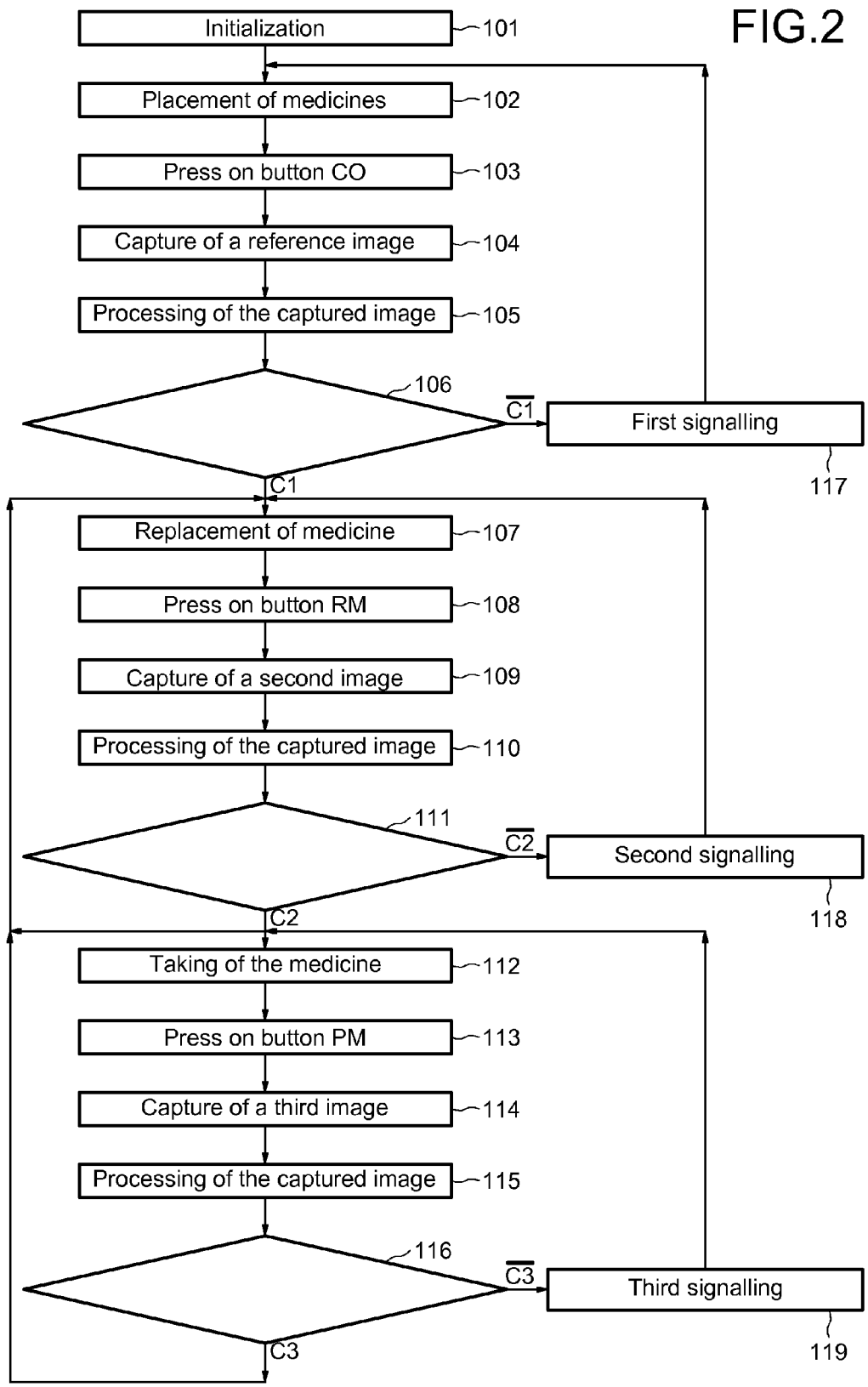
FIG. 2 schematically illustrates a method for checking the dispensing of medicine.

FIG. 2 illustrates the main steps of one implementation of a method for checking the taking of medicines. These steps are also described with reference to FIG. 3 which represents one embodiment.

After a first initialization step (step 101) and the first placement by the user of the medicines (102), in a vessel, a first image is captured (104). The user may, for example, be a pharmacist, a doctor, a nurse, or the patient himself. This first image is called reference image because, as will be indicated below, the validation of the posology will be performed according to the processing of this first image.

In the case where the vessel comprises a number of compartments 320 used to receive the objects to be detected, as is illustrated in FIG. 1, the image capture step is performed for each of the compartments. Each compartment (morning, midday, evening) of each of the drawers (Monday, Tuesday, Wednesday, Thursday, Friday, Saturday, Sunday) is situated under the image capture means 301. For example, the image capture means may be of monochrome or color type.

The photographing of the compartments and the identification of the compartments are carried out by control means 311 according to information from the input means 302.

For example, in the case of a system with drawers, the input means 302 comprise a system of degree-of-opening sensors placed on each of the drawers to deduce therefrom the position of a compartment of a drawer relative to the image capture means 301. A complementary image processing system makes it possible to determine the height of the vessel to deduce therefrom the corresponding day.

According to another example, the day and the timeband may also be entered by the user by means of touching the input means.

The capture of the reference image for each compartment can be triggered via the control means 311 by pressing on a dedicated button CO (step 103) of the input means 302. The capture of the reference image may also be triggered via the control means 311 by the system of degree-of-opening sensors of the input means.

Following the capture of the reference image or images (step 104) by the capture means 301, a processing step is performed on each of the images (step 105).

Figure 3:
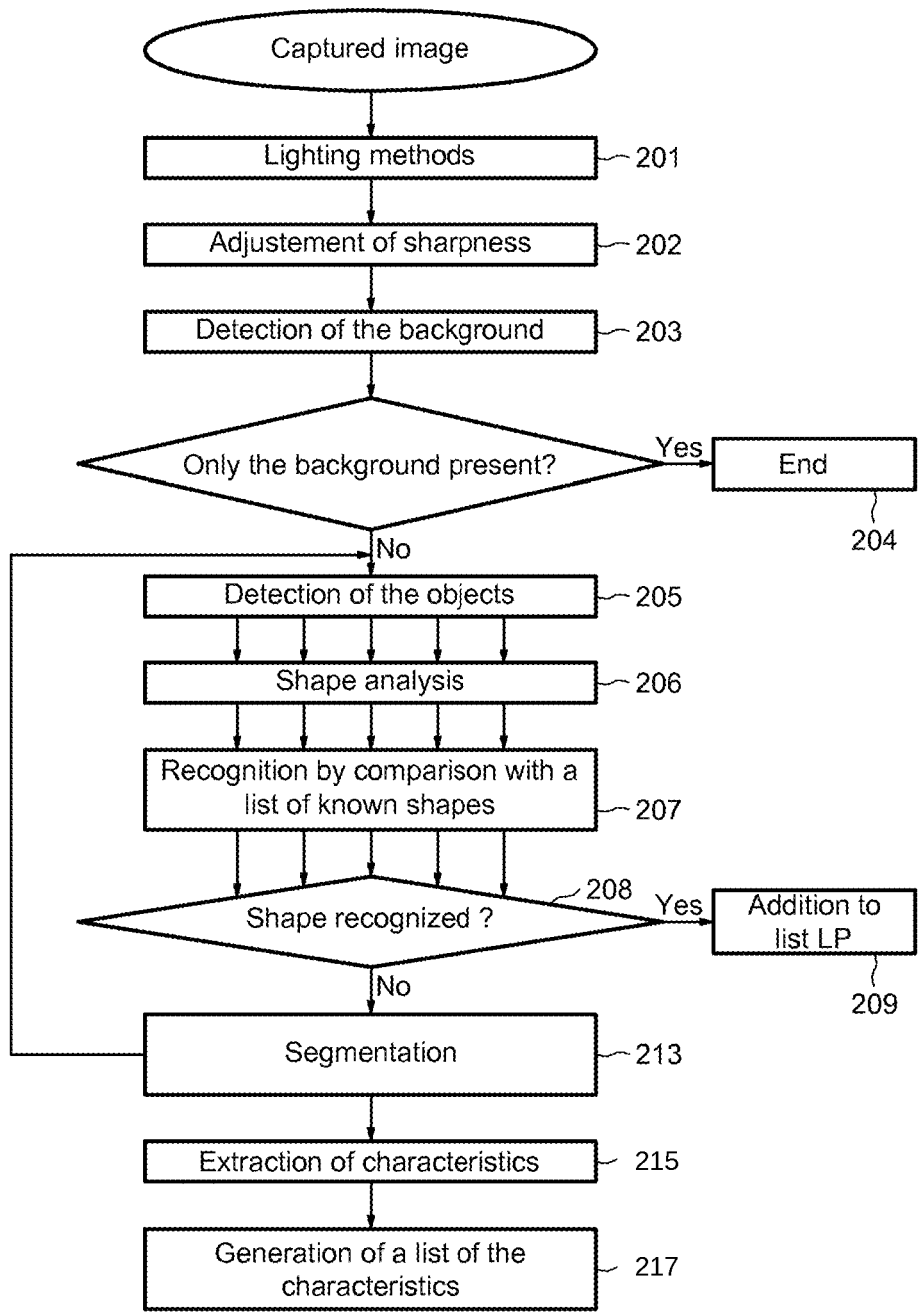
FIG. 3 illustrates an image processing method according to the invention.
Figure 4:
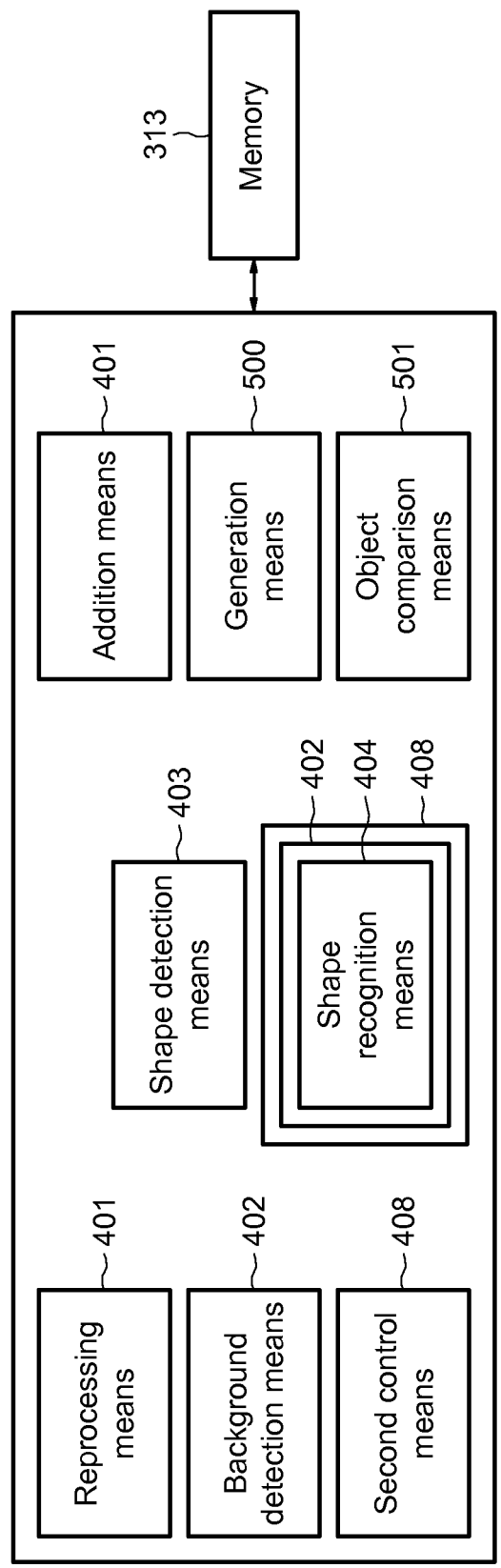
FIG. 4 illustrates one embodiment of the processing system.

The steps of the processing method are illustrated in FIG. 3 and the implementation means are described in FIG. 4.

In order to improve the computation steps during captured image processing operations, it is possible to perform steps 201, 102 for preprocessing the captured image beforehand.

For example, it is possible to make a lighting correction on the captured image (step 201). Then, for example, the sharpness is corrected (step 202). These two steps are performed by the preprocessing means 401. The preprocessing means 401 may also, for example, be configured to make corrections to the colors and the contrast of the captured image.

Then, the detection means 402 perform a background detection (step 203). According to this step, if, in the image, only a background is detected, then the second control means interrupt the processing (step 204). In the contrary case, shape detection means 403 perform steps for object detection (step 205) and shape analysis (step 206). The object detection step (step 205) comprises a region detection which consists in searching for detected pixels and an agglomeration of the similar and adjacent pixels. The processing of an image also comprises a shape analysis step (step 206). This shape analysis 206 and the subsequent steps are performed independently on each of the detected regions. This is illustrated in FIG. 3 by the numerous vertical arrows.

Then, the recognition means 404 perform a step (step 208) for recognizing these shapes by comparison with a list of characteristics of known objects. As an exemplary embodiment, said list of characteristics of known objects is stored in the memory 313. This list of known objects comprises, for example, a square, a circle, an equilateral triangle, a half-disc, and a number of other oblong and semi-oblong shapes. In practice, in the case of conventional medicines which must be placed appropriately by the user, that is to say without stacking, the objects that do not observe these criteria are not medicines or are medicines balanced on an edge or stacked with other medicines. Furthermore, this list of characteristics of known objects comprises, for each known object, different characteristics. These characteristics may be shape characteristics, such as, for example, an object width, a height, an object diameter; or colorimetric characteristics, such as, for example, a tint, a contrast, a luminance, a color; or even object type characteristics, such as, for example, a square, a circle, an ellipse, etc.

It may be noted that this list of characteristics of known objects is also a list of objects because it comprises characteristics of a number of known objects.

During this shape recognition step 208, if a detected region whose analyzed shape is recognized by a comparison of objects, then the addition means 405 add, to a list of medicines LP, the detected object, considered to be a recognized object, whose shape is recognized (step 209), as well as all the extracted characteristics, such as, for example, the geometrical shape, the size, the color, etc.

The comparison of objects consists in comparing the characteristics of the detected objects with, respectively, the characteristics of each object of the list of characteristics of known objects.

This comparison of objects is differentiated from a simple comparison of images by the images being compared pixel by pixel.

This list of medicines LP is a list of characteristics of the detected objects, also denoted list of detected objects. This list of medicines LP is generated following a step for extraction of the characteristics of the detected objects 215.

The list LP is, for example, stored in the memory 313.

In the case where the shape recognition could not culminate on the region detected and analyzed, then, when possible, the segmentation means 406 perform a segmentation (step 213) on said region to identify the recognized objects and the unrecognized objects. For this, the region is, for example, split into two and the processing operations are performed independently on the two regions.

Following the segmentation step 213, the means for extracting characteristics 407 extract as many characteristics as possible (step 215) from the recognized region. Furthermore, the means for extracting characteristics are also configured to extract characteristics from the unrecognized and non-segmentable region, and in this case these characteristics can be used to identify objects that have complex characteristics.

Then, a step 217 for generation of the list of medicines LP is performed, said list comprising the list of each detected object, recognized or unrecognized, and their characteristics extracted in the preceding extraction step 215.

Following this processing operation, a test 106 is then carried out by the control means 311. If there is at least one element in the list LP then a signal (step 117) is indicated to the user. The signaling is performed by signaling means 303 and is triggered by the control means 311. As an exemplary embodiment, these signaling means may be a loudspeaker or an LCD screen. They may also comprise a touch sensitive screen and, in this case, the signaling means are also the input means 302.

With this signal, the user is prompted to ensure that all the medicines are correctly placed (not balanced, not stacked) for example by gently knocking the vessel. It is also possible to consider actuating a vibrator incorporated in the device to modify the position of the medicines. It is also possible to modify the lighting, by adjusting lighting means 304, and to capture another image to improve the identification of the medicines. It is also possible to use the audible warning so that the user can manually modify the position of the medicines. If these modifications still do not make it possible for the unrecognized object or objects to be recognized, these unrecognized objects are then considered as complex objects.

The method then continues with the step 104.

In the case where the conditions C1 of the test are satisfied, that is to say, if there is at least one element in the list LP, then this list LP is stored in the memory 313 by the control means 311 which trigger the continuation of the method.

In order to check that the user has correctly filled the vessel, that is to say, when he replaces the medicines in the vessel, a second image of the vessel is captured, said second image is processed to establish a second list of characteristics, or of objects, and the objects of this second list are compared with the objects of the first list established from the reference image. This comparison of objects is performed, by a comparison of the characteristics of the objects of the second list with, respectively, the characteristics of each object of the first list.

In particular, after the medicines have been replaced in each of the compartments of the vessel, a capture of a second image (step 109) is performed following the triggering (step 108) by the control means via the input means 302. For example, the input means comprise a third dedicated button RM. Then, the second captured image is processed by the processing means 312. The processing operation is identical to the one performed previously. Following this processing operation, a comparison of objects 111 is triggered by the control means 311. This comparison of objects 111 makes it possible to validate whether the posology is correct, that is to say, whether the user has filled the compartments with the medicines corresponding to those of the reference image.

During this comparison of objects 111, the objects of the image that has just been captured are compared with the objects of the first list. If the second list is empty or is not identical to the first list of objects, then the replacement of the medicines is not correct. The control means 311 trigger the signaling means. With this second signal, the user is prompted to ensure that the replacement of medicines is correct, for example, by correctly placing all the necessary medicines or by removing the surplus or even by ensuring that all the medicines are correctly placed (not in balance, not stacked), for example by gently knocking the vessel. The method then continues with the step 112.

In the case where the conditions C2 of the comparison of objects 111 are satisfied, that is to say, if the second list is not empty and if it corresponds to the list of objects of the first list, that is to say that the objects of the second list are identical to the objects of the first list, then the method continues with the medicine-taking step (step 112).

The step 112 corresponds to the step of taking of the medicine by the user from a compartment of the vessel. For this, the drawer of the corresponding day must be opened and the timeband is placed facing the capture means. After the medicine has been taken, the input means trigger the capture of a third image. To this end, the input means may comprise a dedicated button PM. The input means may also comprise a system of degree-of-opening sensors placed on each of the drawers as indicated previously.

Then, the third captured image is processed by the processing means 312. The processing operation is identical to the one performed previously. Following this processing operation, a comparison of objects 116 is triggered by the control means 311. If there is at least one object in the third list, then a third signal (step 119) is indicated to the user. To this end, the control means 311 also trigger the signaling means 303. With this third signal, the user is prompted to ensure that the compartment is indeed empty by, for example, finishing all the medicines in the compartment.

In the case where the conditions C2 of the comparison of objects are satisfied, that is to say, if the third list is not empty, then the method continues according to two alternatives. Either there are still compartments from which the user must take his medicines and the medicine-taking step 112 is repeated, or the takings of medicines have been performed and the dispenser must be refilled. To this end, the medicine-replacement step 107 is performed once again.

The methods of FIGS. 2 and 3 are respectively implemented in the control means 311 and in the processing means 312.

FIGS. 1 and 4 illustrate an architecture according to which the image capture means 301, the input means 302, the signaling means 303, and the ECU (electronic control unit) cooperate to perform the check on the dispensing of the medicines. The ECU comprises the control means 311, the memory 313 and the image processing means 312. The latter comprise the preprocessing means 401, the background detection means 402, the second control means 408, the shape recognition means 404, the detection means 403, the addition means 401, the segmentation means 402 and the characteristics extraction means 408.

The means mentioned hereinabove are all incorporated in the device for detecting objects 1, which renders the device independent of any external additional checking system.

The means mentioned hereinabove can be implemented in the form of software modules, for example, in one or more computers.

Figure 5:
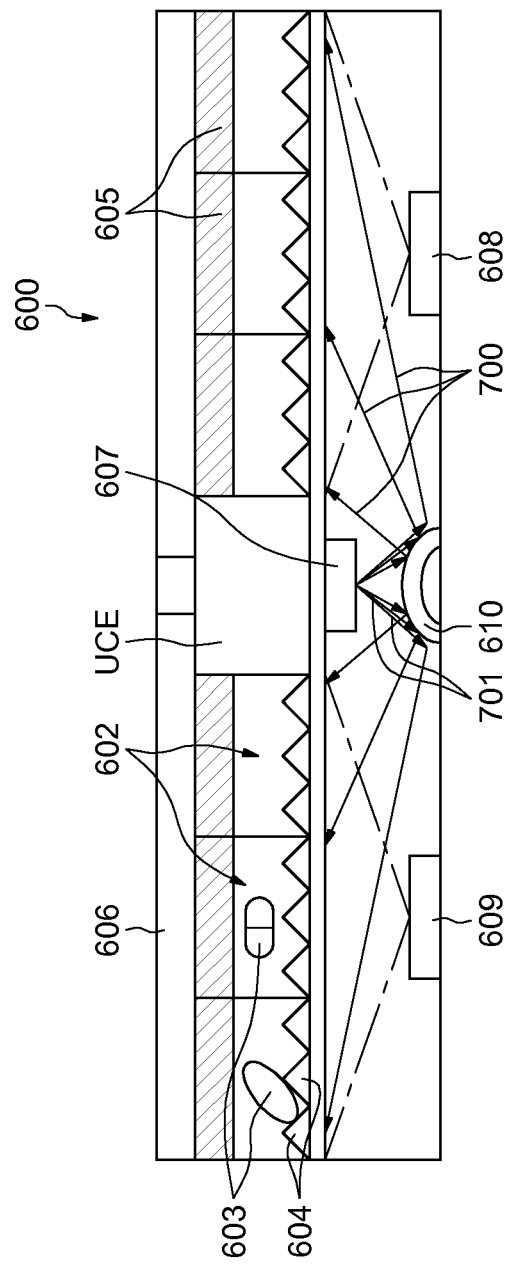
FIG. 5 illustrates another embodiment of the object detection device.

FIG. 5 shows another embodiment of a device for detecting objects 600. This device 600 comprises a vessel 601 that has a number of compartments 602 intended to receive medicines 603. The compartments 602 are provided with a bottom which is transparent and which has surface irregularities 604, pyramidal for example. These surface irregularities make it easier to separate the medicines and make it possible to make the image processing simpler and more reliable.

Moreover, the compartments 602 include a patterned foam 605 for wedging the medicines and making it easier to extract the bottom of the vessel during image processing.

Furthermore, the device 600 comprises a rotary lid 606 which includes a total opening, that is to say, one which opens all the compartments 602, for the filling of the vessel 601 and an opening for each compartment for the daily taking of medicines.

The device 600 is also fitted with a single fixed camera 607, lighting systems 608, 609 for lighting under the vessel 601 and for lighting the compartments 602 through their transparent bottom, and an optical system 610, for example a spherical mirror, which makes it possible to limit the height of the device 600, while allowing said camera 607 to take an image of the objects of all the compartments of the vessel.

Also shown are the light paths 700, 701 between the compartments 602 and the optical system 610 on the one hand, and between the optical system 610 and the camera 607 on the other hand.

Thus, the device 600 has a height which can be low and which makes it possible to manufacture a device 600 with little bulk, for example which may be carried in a pocket of a user.

The device 600 also comprises a ECU comprising control means, processing means and a memory described in the preceding FIGS. 2 to 4.

In particular, this device 600 operates in any position since the medicines are wedged with the help of the foams and the image capture can be done in all positions.

Thus, a device for detecting objects that is portable is provided, that is to say, one that has a small size and low weight, designed to be easily carried about the person, in the pocket for example.

According to possible enhancements of the invention, during the image processing operations, color may also be used, allowing for simpler region detection and segmentation steps.

The reference to "means" herein refers to any suitable device, circuit, apparatus, and the like configured to perform the recited function. Such devices, circuits, apparatus, and the like are known to those skilled in the art. As example, the input means may comprise any suitable input device such as button, switch, touch pad, key pad, etc. The signaling means may comprise any suitable signaling device, for example, providing for audible or visual signaling, such as a light, buzzer, display, etc. The image capture means may comprise any suitable imaging device such as a camera or matrix photosensor device. The ECU is configured with appropriate control circuitry and processing circuitry, as well as control processing software, firmware or other programming.

The invention claimed is:

1. A device for detecting objects, comprising:
 a vessel configured to contain the objects to be detected and having a relief bottom;
 an imager configured to capture an image of the vessel;
 a vibration unit for displacing the objects contained in the vessel:,
 a wedging device for wedging the objects in said vessel;
 a processor configured to process said captured image so as to detect first objects in said at least one captured image, extract characteristics of each detected object of the first objects, and generate a list of the characteristics of each detected object of the first objects;
 a memory configured to store said generated list, the memory further configured to store a first reference list of object characteristics; and
 a sensor configured to detect replacement of the first objects in the vessel with second objects in the vessel such that the first objects are no longer in the vessel and to generate a trigger for the processor in response thereto;
 wherein said processor is further configured to, in response to the trigger:
  capture a new image of the vessel as containing the second objects and not the first objects,
  process the new image so as to detect the second objects and not the first objects in the new image, extract characteristics of each detected object of the second objects in the new image, and generate a second list of characteristics from the new image, and
  compare characteristics of each object from the second list with, respectively, the characteristics of each object from the first reference list to determine correspondence between the objects in the new image and the objects in the image.

2. The device according to claim 1, wherein said processing to extract characteristics comprises operation by the processor to segment unrecognized objects out of detected objects and perform a second object detection for each unrecognized object.

3. The device according to claim 2, wherein the memory is configured to store a list of characteristics of known objects, and the operation to segment comprises performing a shape recognition which compares the characteristics of each detected object with, respectively, the characteristics of each known object in order to identify the recognized objects out of the detected objects.

4. The device according to claim 1, further comprising a signaler configured to signal the result of the comparison obtained from the processor.

5. The device according to claim 1, wherein the processor is operable to detect whether at least one object is present within the vessel in a captured image.

6. The device according to claim 5, further comprising a controller configured to interrupt the processor when no object is detected within the vessel.

7. The device according to claim 1, wherein the processor is further configured to preprocess the captured image.

8. The device according to claim 1, wherein the vessel has a dark and matt bottom.

9. The device according to claim 1, wherein the vessel has a bottom comprising a number of identical patterns.

10. The device according to claim 1, wherein the vessel comprises a transparent bottom, the device further comprising a light source arranged under the vessel and configured to light the vessel through a transparent bottom.

11. The device according to claim 10, further comprising a mirror configured to enable said imager to capture an image of said objects to be captured.

12. The device according to claim 1, forming a portable element.

13. The device according to claim 1, wherein said objects are medicinal pills, and said device is operable as a pill dispenser.

14. A method for detecting objects contained in a vessel having a relief bottom, comprising:
 selectively displacing the objects contained in the vessel using a vibration unit;
 wedging the objects contained in the vessel using a wedging device;
 capturing at least one image of the vessel; and
 processing said at least one captured image;
 wherein processing comprises:
  detecting first objects of said at least one first image;
  extracting characteristics of each detected object;
  generating a list of the characteristics of each detected object; and
  storing said list of the characteristics;
 the method further comprising:
  storing a first reference list of object characteristics;
  sensing replacement of the first objects contained in the vessel with second objects such that the first objects are no longer in the vessel;
  capturing at least one new image of the vessel as containing the second objects and not the first objects in response to sensing of the replacement of the first objects with the second objects;
  processing said new captured image so as to detect the second objects and not the first objects in the at least one new image and generate a second list of characteristics of each detected object of the second objects; and comparing the characteristics of each object of the second list with, respectively, the characteristics of each object of the first reference list.

15. The method according to claim 14, wherein processing comprises:
segmenting unrecognized objects out from detected objects; and
performing a second object detection for each unrecognized object.

16. The method according to claim 15, further comprising:
storing a list of characteristics of known objects; and
wherein processing comprises performing a shape recognition by comparing the characteristics of each detected object with, respectively, the characteristics of each known object, in order to identify the recognized objects out of the detected objects.

17. The method according to claim 16, further comprising: signaling a result of the comparison.

18. The method according to claim 17, further comprising:
first signaling if at least one object of said image captured so as to store a second list of characteristics is unrecognized, and
second signaling if, following a comparison of the characteristics of each object of the second list with, respectively, the characteristics of each object of the reference list, at least one object of the second list is different from the objects of the reference list.

19. The method according to claim 18, further comprising:
displacing objects contained in the vessel following said first signaling;
capturing a new image;
processing said new captured image so as to store a new list of characteristics; and
comparing objects comprising a comparison of the characteristics of each object of the new list with, respectively, the characteristics of each object of the reference list.

20. The method according to claim 19, further comprising:
capturing another image of the vessel;
processing said another image comprising a detection of the background of the vessel; and
a third signaling if at least one object is detected within the vessel in said other processed image.

21. The method according to claim 14, wherein processing comprises: detecting a background of the vessel; and interrupting processing when no object is detected within the vessel.

22. The method according to claim 14, wherein processing further comprises preprocessing said at least one captured image.

* * * * *